United States Patent [19]

Nishida et al.

[11] Patent Number: 5,300,662
[45] Date of Patent: Apr. 5, 1994

[54] PROCESS FOR PRODUCING COUMARIN AND DERIVATIVES THEREOF

[75] Inventors: Yoshitaka Nishida; Kiyomi Sakai; Tamio Shirafuji, all of Ehime, Japan

[73] Assignee: Sumitomo Chemical Company, Limited, Osaka, Japan

[21] Appl. No.: 966,345

[22] Filed: Oct. 26, 1992

[30] Foreign Application Priority Data

Oct. 24, 1991 [JP] Japan .................................. 3-277688

[51] Int. Cl.$^5$ ................... C07D 311/14; C07D 311/16
[52] U.S. Cl. ...................................................... 549/290
[58] Field of Search ......................................... 549/290

[56] References Cited

U.S. PATENT DOCUMENTS 3,442,910  5/1969  Thweatt .............................. 549/290
3,856,819 12/1974  Deumens et al. ................... 549/290

OTHER PUBLICATIONS

Chemical Abstracts, vol. 116, No. 1, Jan. 6, 1992, Columbus, Ohio, Abstract No. 6415z, K. Oknumua et al.; Preparation of Coumarin Derivatives' p. 636 and JPA-3 197 478 (Fuso Chemical) Aug. 28, 1991.

*Primary Examiner*—C. Warren Ivy
*Assistant Examiner*—Ba K. Trinh
*Attorney, Agent, or Firm*—Sughrue, Mion, Zinn, Macpeak & Seas

[57] ABSTRACT

A process for producing coumarin or a derivative thereof, which process comprises dehydrogenation of 3,4-dihydrocoumarin or a derivative thereof in the presence of a palladium catalyst by heating under reduced pressure.

14 Claims, No Drawings

PROCESS FOR PRODUCING COUMARIN AND DERIVATIVES THEREOF

FIELD OF THE INVENTION

This invention relates to a process for producing coumarin or a derivative thereof from 3,4-dihydrocoumarin or a derivative thereof. Coumarin is an important compound in the perfume industry and is also useful as an intermediate for dyes, agricultural chemicals or pharmaceuticals.

BACKGROUND OF THE INVENTION

Known processes for obtaining coumarin or a derivative thereof include cyclization and dehydrogenation of a 3-(2-cyclohexanoyl)propionic acid ester or a derivative thereof in the presence of a hydrogenation-dehydrogenation catalyst, e.g., palladium, as disclosed in U.S. Pat. No. 3,442,910 or in the presence of a noble metal catalyst, e.g., palladium, in combination with a co-catalyst, such as barium sulfate or nickel oxide, as disclosed in JP-A-60-181082 (the term "JP-A" as used herein means an "unexamined published Japanese patent application").

It is also known to obtain coumarin or a derivative thereof by dehydrogenation of 3,4-dihydrocoumarin or a derivative thereof in the presence of a noble metal catalyst, such as palladium, as disclosed in Ber., 70B, pp. 735-738 (1936) or by using chlorine, bromine, oxygen, or sulfur as disclosed in Monatsh., Vol. 34, pp. 1671-1672 (1913) and German Patent 276,667.

The cyclization and dehydrogenation of a 3-(2-cyclohexanoyl)propionic ester in the presence of a palladium catalyst under heating does not always attain a high yield of coumarin and is accompanied with by-production of 3,4-dihydrocoumarin in a large proportion. The dehydrogenation of 3,4-dihydrocoumarin using chlorine, sulfur, etc. meets difficulty in removing the chlorine or sulfur, etc. from the reaction mixture and therefore involves complicated purification steps.

The dehydrogenation of 3,4-dihydrocoumarin in the presence of a palladium catalyst has an advantage of relatively easy purification. However, hydrogen which is by-produced by the dehydrogenation concurrently induces hydrogenation of coumarin produced into 3,4-dihydrocoumarin, the dehydrogenation as purposed does not always proceed sufficiently, and the yield of coumarin is not so high as expected.

SUMMARY OF THE INVENTION

An object of the present invention is to provide a process for producing coumarin or a derivative thereof from 3,4-dihydrocoumarin or a derivative thereof in a high yield.

As a result of extensive investigation, it has now been found that the yield of coumarin in dehydrogenation of 3,4-dihydrocoumarin can be greatly increased by carrying out the dehydrogenation by heating under reduced pressure. The present invention has been completed based on this finding.

The present invention relates to a process for producing coumarin or a derivative thereof represented by formula (2):

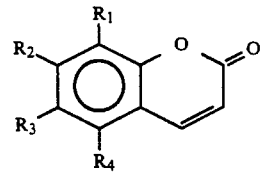

wherein $R_1$, $R_2$, $R_3$, and $R_4$ each represent a hydrogen atom, a methyl group, or an ethyl group, provided that at least two of them are hydrogen atoms, which process comprises the step of: dehydrogenating 3,4-dihydrocoumarin or a derivative thereof represented by formula (1):

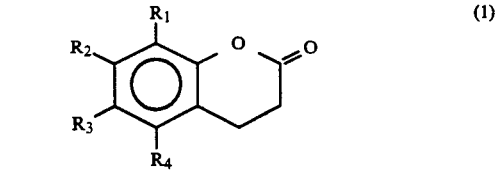

wherein $R_1$, $R_2$, $R_3$, $R_4$ are as defined above, in the presence of a palladium catalyst by heating under reduced pressure.

DETAILED DESCRIPTION OF THE INVENTION

Examples of the 3,4-dihydrocoumarin or a derivative thereof which can be used in the present invention includes 3,4-dihydrocoumarin, 5-methyl-3,4-dihydrocoumarin, 6-methyl-3,4-dihydrocoumarin, 7-methyl-3,4-dihydrocoumarin, 8-methyl-3,4-dihydrocoumarin, 5-ethyl-3,4-dihydrocoumarin, 6-methyl-3,4-dihydrocoumarin, 7-ethyl-3,4-dihydrocoumarin, 8-methyl-3,4-dihydrocoumarin, 5,6-dimethyl-3,4-dihydrocoumarin, 5,7-dimethyl-3,4-dihydrocoumarin, 5,8-dimethyl-3,4-dihydrocoumarin, 6,7-dimethyl-3,4-dihydrocoumarin, 6,8-dimethyl-3,4-dihydrocoumarin, 7,8-dimethyl-3,4-dihydrocoumarin, 5-methyl-6-ethyl-3,4-dihydrocoumarin, 5-methyl-7-ethyl-3,4-dihydrocoumarin, 5-methyl-8-ethyl-3,4-dihydrocoumarin 6-methyl-7-ethyl-3,4-dihydrocoumarin, 6-methyl-8-ethyl-3,4-dihydrocoumarin, 7-methyl-8-ethyl-3,4-dihydrocoumarin 5-ethyl-6-methyl-3,4-dihydrocoumarin, 5-ethyl-7-methyl-3,4-dihydrocoumarin, 5-ethyl-8-methyl-3,4-dihydrocoumarin, 6-ethyl-7-methyl-3,4-dihydrocoumarin, 6-ethyl-8-methyl-3,4-dihydrocoumarin, and 7-ethyl-8-methyl-3,4-dihydrocoumarin. However, the 3,4-dihydrocoumarin or a derivative thereof is not limited to these examples.

The palladium catalyst which can be used in the present invention is a solid metallic catalyst comprising palladium supported on at least one carrier selected from the group consisting of an element of Group IIA, IIIA, IVA or VIA and a compound thereof, e.g., carbon, alumina, silica gel, and barium sulfate. The catalyst can be prepared by a known method, for example, an impregnation method described in Shokubai Jikken Manual (Catalyst Experiment Manual) edited by Shokubai Gakkai, published by Maki Shoten, Japan, which comprises impregnating a metal into a carrier followed by reduction in hydrogen at a high temperature. A commercially available palladium-on-carbon catalyst may be used as such. The catalyst can be repeatedly used.

The catalyst is used in an amount usually of about from 0.005 to 0.25% by weight, and preferably from 0.01 to 0.15% by weight, in terms of metallic palladium based on the amount of 3,4-dihydrocoumarin or a derivative thereof. Too a small amount of the catalyst exerts considerably reduced reaction activity, and too a large amount has excessive reaction activity to give much by-products.

The starting 3,4-dihydrocoumarin or its derivative used in the present invention is generally those obtained by cyclization and dehydrogenation of a 3-(2-cyclohexanoyl)propionic ester or its derivative in the presence of a palladium catalyst followed by separating coumarin or its derivative from the reaction mixture by distillation. However, the starting material is not limited thereto, and 3,4-dihydrocoumarin or its derivative produced by any method can be used in the present invention.

The reaction of the present invention is carried out under reduced pressure, preferably at about from 300 to 700 Torr. Although the reason for the effectiveness of conducting the reaction under reduced pressure is not clear, it is considered that the hydrogen resulting from the dehydrogenation is forcedly driven out of the reaction system and is thus prevented from reacting with the produced coumarin.

The dehydrogenation of the present invention is carried out in a temperature ranging usually about from 100° to 300° C., and preferably about from 200° to 270° C. The upper limit of the reaction temperature varied depending on the reaction pressure. While the reaction temperature is lower than that employed in the reactions under normal pressure, it is preferable to conduct the reaction at a temperature elevated as high as possible under a fully refluxing condition.

The dehydrogenation may be performed in a solvent. Examples of the solvents include phenyl ether, benzyl ether, methyl α-naphthyl ether, ethylnaphthalene, dimethylbiphenyl, dodecane, tetradecane, tetralin, acetophenone, phenyl propyl ketone, methyl benzoate, and dimethyl glutamate. The amount of the solvent is generally about from 0.5 to 10 times by weight the amount of 3,4-dihydrocoumarin or its derivative.

The dehydrogenation is usually continued at prescribed temperature and pressure for about from 5 to 50 hours, preferably about from 10 to 30 hours.

The process according to the present invention achieves a markedly increased yield as compared with the conventional techniques and has a great industrial value.

The present invention is now illustrated in greater detail with reference to Examples, but it should be understood that the present invention is not construed as being limited thereto. All the percents are by weight unless otherwise indicated.

EXAMPLE 1

In a four-necked flask were charged 200 g of 3,4-dihydrocoumarin and 2.0 g of a 50% hydrated catalyst composed of 5% palladium on activated carbon. The mixture was heated in a nitrogen atmosphere at 250° C. under 600 Torr for 15 hours with stirring at 500 rpm. After completion of the reaction, the catalyst was recovered by filtration. Gas chromatography analysis of the filtrate revealed that the coumarin yield was 52.1 mol % based on the charged 3,4-dihydrocoumarin.

EXAMPLE 2

Dehydrogenation of 3,4-dihydrocoumarin was conducted in the same manner as in Example 1, except for changing the reaction conditions to 230° C. and 450 Torr. As a result, the coumarin yield was 65.4 mol % based on the charged 3,4-dihydrocoumarin.

COMPARATIVE EXAMPLE 1

Dehydrogenation of 3,4-dihydrocoumarin was conducted in the same manner as in Example 1, except for changing the reaction conditions to 270° C. and normal pressure. As a result, the coumarin yield was 41.4 mol % based on 3,4-dihydrocoumarin.

While the invention has been described in detail and with reference to specific examples thereof, it will be apparent to one skilled in the art that various changes and modifications can be made therein without departing from the spirit and scope thereof.

What is claimed is:

1. A process for producing coumarin or a derivative thereof represented by formula (2):

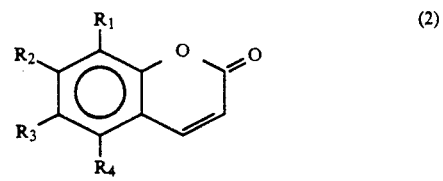

(2)

wherein $R_1$, $R_2$, $R_3$, and $R_4$ each represents a hydrogen atom, a methyl group, or an ethyl group, provided that at least two of $R_1$, $R_2$, $R_3$, and $R_4$ are hydrogen atoms,
said process comprising the step of: dehydrogenating 3,4-dihydrocoumarin or a derivative thereof represented by formula (1):

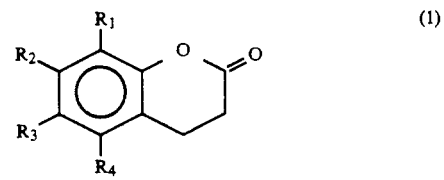

(1)

wherein $R_1$, $R_2$, $R_3$, and $R_4$ are as defined above, in the presence of a palladium catalyst by heating at a pressure of 300 to 700 Torr.

2. A process as claimed in claim 1, wherein said 3,4-dihydrocoumarin or a derivative thereof is 3,4-dihydrocoumarin.

3. A process as claimed in claim 1, wherein said 3,4-dihydrocoumarin or a derivative thereof is 3,4-dihydrocoumarin or a derivative thereof obtained by cyclization and dehydrogenation of a 3-(2-cyclohexanoyl)-propionic acid ester or a derivative thereof, followed by separation of coumarin or a derivative thereof.

4. A process as claimed in claim 1, wherein said palladium catalyst is present in an amount of about from 0.005 to 0.25% by weight in terms of metallic palladium based on the amount of said 3,4-dihydrocoumarin or derivative thereof.

5. A process as claimed in claim 1, wherein the heating temperature is from about 100° to 300° C.

6. A process as claimed in claim 5, wherein the heating temperature is from about 200° to 270° C.

7. A process as claimed in claim 1, wherein the 3,4-dihydrocoumarin derivative is selected from the group consisting of 5-methyl-3,4-dihydrocoumarin, 6-methyl-3,4-dihydrocoumarin, 7-methyl-3,4-dihydrocoumarin, 8-methyl-3,4-dihydrocoumarin, 5-ethyl-3,4-dihydrocoumarin, 6-ethyl-3,4-dihydrocoumarin, 7-ethyl-3,4-dihydrocoumarin, 8-ethyl-3,4-dihydrocoumarin, 5,6-dimethyl-3,4-dihydrocoumarin, 5,7-dimethyl-3,4-dihydrocoumarin, 5,8-dimethyl-3,4-dihydrocoumarin, 6,7-dimethyl-3,4-dihydrocoumarin, 6,8-dimethyl-3,4-dihydrocoumarin, 7,8-dimethyl-3,4-dihydrocoumarin, 5-methyl-6-ethyl-3,4-dihydrocoumarin, 5-methyl-7-ethyl-3,4-dihydrocoumarin, 5-methyl-8-ethyl-3,4-dihydrocoumarin, 6-methyl-7-ethyl-3,4-dihydrocoumarin, 6-methyl-8-ethyl-3,4-dihydrocoumarin, 7-methyl-8-ethyl-3,4-dihydrocoumarin, 5-ethyl-6-methyl-3,4-dihydrocoumarin, 5-ethyl-7-methyl-3,4-dihydrocoumarin, 5-ethyl-8-methyl-3,4-dihydrocoumarin, 6-ethyl-7-methyl-3,4-dihydrocoumarin, 6-ethyl-8-methyl-3,4-dihydrocoumarin and 7-ethyl-8-methyl-3,4-dihydrocoumarin.

8. A process as claimed in claim 1, wherein said palladium catalyst comprises palladium supported on a carrier comprising an element or compound of an element of Groups IIA, IIIA, IVA or VIA of the Periodic Table.

9. A process as claimed in claim 4, wherein said palladium catalyst is present in an amount of about from 0.01 to 0.15% by weight in terms of metallic palladium based on the amount of said 3,4-dihydrocoumarin or derivative thereof.

10. A process as claimed in claim 1, wherein said dehydrogenation is carried out in the presence of a solvent.

11. A process as claimed in claim 10, wherein said solvent is selected from the group consisting of phenyl ether, benzyl ether, methyl α-naphthyl ether, ethylnaphthalene, dimethylbiphenyl, dodecane, tetradecane, tetralin, acetophenone, phenyl propyl ketone, methyl benzoate and dimethyl glutamate.

12. A process as claimed in claim 10, wherein said solvent is present in an amount of about from 0.5 to 10 times by weight the amount of said 3,4-dihydrocoumarin or derivative thereof.

13. A process as claimed in claim 1, wherein said dehydrogenation is carried out for about from 5 to 50 hours.

14. A process as claimed in claim 13, wherein said dehydrogenation is carried out for about from 10 to 30 hours.

* * * * *

UNITED STATES PATENT AND TRADEMARK OFFICE
CERTIFICATE OF CORRECTION

PATENT NO. : 5,300,662
DATED : April 5, 1994
INVENTOR(S) : Yoshitaka Nishida et al.

It is certified that error appears in the above-indentified patent and that said Letters Patent is hereby corrected as shown below:

Column 1, lines 30-31, change "pp. 735-738 (1936)" to -- pp. 235-238 (1937) --.

Column 1, lines 32-33, change "pp. 1671-1672" to -- pp. 1665-1672. --.

Signed and Sealed this

Thirtieth Day of July, 1996

Attest:

BRUCE LEHMAN

Attesting Officer    Commissioner of Patents and Trademarks